United States Patent [19]
Springmann et al.

[11] Patent Number: 4,625,057
[45] Date of Patent: Nov. 25, 1986

[54] PROCESS FOR THE PRODUCTION OF CARBOXYMETHYLATED ALCHOLS, ETHER ALCOHOLS, THIOALCOHOLS, OR ALKYL PHENOLS

[75] Inventors: Hermann Springmann, Haltern; Kurt Kosswig, Marl, both of Fed. Rep. of Germany

[73] Assignee: Huels Aktiengesellschaft, Marl, Fed. Rep. of Germany

[21] Appl. No.: 522,771

[22] Filed: Aug. 12, 1983

[30] Foreign Application Priority Data

Aug. 18, 1982 [DE] Fed. Rep. of Germany ....... 3230677

[51] Int. Cl.$^4$ .............................................. C07C 59/48
[52] U.S. Cl. .................... 562/470; 562/471; 562/588; 562/581
[58] Field of Search ................ 562/470, 471; 562/588

[56] References Cited

U.S. PATENT DOCUMENTS 2,509,772  5/1950  Leaper ................................. 562/471
2,623,900  12/1952  Hofer .................................. 562/470
2,805,251  9/1957  Marshall .............................. 562/471
3,992,443  11/1976  Springmann ......................... 562/588

FOREIGN PATENT DOCUMENTS 1153762  9/1963  Fed. Rep. of Germany ...... 562/470
2759169  7/1979  Fed. Rep. of Germany ...... 562/588
50-24215  3/1975  Japan .................................. 562/471

Primary Examiner—Paul J. Killos
Attorney, Agent, or Firm—Millen & White

[57] ABSTRACT

A process for the production of carboxymethylates comprises reacting alcohols, ether alcohols, or alkyl phenols with an aqueous solution of at most a stoichiometric amount of free chloroacetic acid and twice the stoichiometric amount of an aqueous base. The chloroacetic acid and base are added separately, but simultaneously under agitation (at elevated temperature and under reduced pressure) to the alcohol or alkyl phenol. The water content in the reaction mixture, during the entire reaction, is maintained at 0.3–1.5% by weight. Increased selectivity results and it now becomes possible to use aqueous chloroacetic acid in this process.

17 Claims, No Drawings

PROCESS FOR THE PRODUCTION OF CARBOXYMETHYLATED ALCHOLS, ETHER ALCOHOLS, THIOALCOHOLS, OR ALKYL PHENOLS

BACKGROUND OF THE INVENTION

The present invention relates to an improved process for the production of carboxymethylated alcohols or phenols, and in particular, of polyether alcohols.

The carboxymethylated alcohols and ether alcohols are compounds of the type $R(OCH_2CH_2)_n-X-CH_2COOH$ which, $X=O$, S with appropriate selection of the residue R and of the degree of oxethylation n, represent valuable tensides (surface active agents) usable, for example, in tertiary oil recovery. (See, e.g., Tenside Detergents 16:256-261 [1979], whose disclosure is incorporated by reference herein).

A conventional method for the preparation of etheric carboxylic acids or polyether carboxylic acids comprises first obtaining the corresponding alcoholates from an alcohol or ether alcohol, respectively, and an alkali metal hydroxide, and thereafter carboxymethylating these products with sodium chloroacetate (See, e.g., U.S. Pat. No. 2,623,900). A substantial improvement in this process has been disclosed in more recent literature. According to U.S. Pat. No. 3,992,443, the polyether alcohol is mixed with sodium chloroacetate and an equivalent amount of sodium hydroxide is added to this mixture either in the form of a powder or as an aqueous, approximately 50% strength solution; in the latter case, the water introduced is simultaneously removed from the reaction mixture as exhaustively as possible (cf. Example 5 thereof).

A very similar mode of operation is disclosed in Japanese Patent Application No. Sho-50-24 215 of Kao Sekken K.K.

In both literature references, the attainable degree of conversion to the correspondingly carboxymethylated compounds is indicated as about 90 molar percent if the process is carried out with a molar ratio of oxethylate:chloroacetate of 1:1. (See U.S. Pat. No. 3,992,443, Example 5; and No. Sho-50-24 215, Examples 1 and 2.) If still higher degrees of conversion are demanded, this can only be attained by using a considerable excess (20-50%) of chloroacetate as compared with the alcohol or ether alcohol (see U.S. Pat. No. 3,992,443, column 3, lines 1-6). In Example 11 of this patent, a total of 2.25 moles of sodium chloroacetate is used per 1.5 moles of oxethylate, to obtain a degree of conversion of 98.6% into the desired carboxylic acid. In addition, another drawback involves the long reaction period of about 36 hours required to reach this degree of conversion.

SUMMARY OF THE INVENTION

Therefore, it is an object of the present invention to provide a process of carboxymethylation so that a maximally quantitative conversion of the chloroacetate into the desired carboxymethylated product is obtained.

Moreover, it is another object of this invention to provide such a process which operates, on the whole, more economically, for instance by using readily dosable components in the liquid phase, facilitating a large-scale technical application of the process.

Thus, it is a primary object of this invention to provide a process making it possible to conduct a quantitative or almost quantitative conversion of the chloroacetic acid used in the carboxymethylation reaction into the corresponding carboxylates in a way that is readily feasible from an industrial viewpoint.

Upon further study of the specification and appended claims, further objects and advantages of this invention will become apparent to those skilled in the art.

These objects have been attained by providing a process for the production of carboxymethylated alcohols, ether alcohols, thioalcohols, or alkyl phenols by reaction between (thio)alcohols, (thio)ether alcohols, or alkyl phenols with a salt of chloroacetic acid and an hydroxide, wherein aqueous solutions of at most once the molar quantity of free monochloroacetic acid and twice the molar quantity of an aqueous base (based on alcohol or phenol), are added separately but simultaneously under agitation at an elevated temperature and under reduced pressure, to a provided, saturated or unsaturated, straight-chain or branched alcohol of 8-20 carbon atoms or a (di)alkyl phenol of 7-18 carbon atoms in the alkyl chain, or an ether alcohol of the formula $R-(OCH_2-CH_2)_n-OH$ wherein R is a saturated or unsaturated, straight-chain or branched aliphatic residue of 8-20 carbon atoms or a (di)alkyl phenyl residue of 7-18 carbon atoms in the alkyl chain, and n is an integer of 1-30; and wherein, during the addition of the reaction components, the water content in the reaction mixture is 0.3-1.25% by weight, preferably 0.3-0.8% by weight.

DETAILED DISCUSSION

The use of aqueous sodium hydroxide solution is disclosed in the state of the art (U.S. Pat. No. 3,992,443, Examples 5 and 6; as well as Japanese Patent Disclosure No. Sho-50-24215). However, the use of an aqueous chloroacetic acid solution is unknown.

Although U.S. Pat. No. 3,992,443 mentions that the free acid can be employed in place of sodium chloroacetate, no detailed instructions are given on how to conduct this process. Among the forms available for commercial shipping, sodium chloroacetate is the most valuable delivery grade, but also most difficult to handle. Free chloroacetic acid is less valuable and must be metered in the molten state, requiring considerable expenditure for heatable containers, pumps, and pipelines. The least valuable form for commercial shipping is an 80% aqueous solution of chloroacetic acid, which can be transported and metered without complications. Therefore, the use of aqueous chloroacetic acid is to be preferred for economic and technical reasons.

It can be seen from the literature that the general consensus considers water to have an extraordinarily negative effect on the course of the carboxymethylation reaction. For example, older references (Dutch Pat. No. 64 534) suggest the binding of the thus-formed water of reaction, by adding calcium carbide, to the reaction mixture. Also, the above-cited more recent patent literature mentions a negative effect exerted by water (U.S. Pat. No. 3,992,443, column 4, lines 1-6). The influence of water is discussed in greater detail in the Japanese Patent Application (No. Sho-50-24 215). A change in reaction pressure at a given temperature affects the water content in the system.

The more the pressure is lowered, i.e. the less water that exists in the reaction system, the more favored is the primary reaction (i.e. the desired reaction); the less the pressure is lowered, the more water will be in the reaction system, and the lesser is the favorable influence exerted on the primary reaction. It is furthermore disclosed that since the reaction is ionic, the total reaction velocity is high if a small amount of water is present. At another place in the patent, the "total reaction velocity" is defined as the rate at which the halocarboxylic acid is being consumed. Thus, if this rate is increased by the presence of water, while on the other hand the primary reaction, viz., the formation of carboxymethylated product, is impaired by water, then the presence of water must promote the undesirable hydrolysis reaction of the halocarboxylic acid and therefore the latter is lost for the desirable primary reaction.

The entire disclosures of U.S. Pat. No. 3,992,443 and Japanese Patent disclosure No. Sho-50-24 215 are incorporated by reference herein.

It has now been surprisingly discovered that these relationships do not apply to a process for the production of carboxymethylated alcohols, ether alcohols, or alkyl phenols and their oxethylates as required by this invention. Although a certain water concentration is maintained, the carboxymethylation reaction is not impaired as would be expected according to the above remarks. Rather, the chloroacetic acid employed reacts with formation of the desired carboxymethylated products and substantially without appreciable formation of glycolic acid due to hydrolysis. The chloroacetic acid employed is reacted with complete conversion to the carboxymethylated compounds with a selectivity of above 90% to almost 100%.

Therefore, a very important element of the novel process of this invention is the maintenance of a water concentration in the reaction mixture within a relatively narrow range. Very short reaction periods are achieved, and the chloroacetic acid employed is utilized for the desired carboxymethylation reaction at a proportion of more than 95%.

It is also possible, for this reason, to use the alkali metal or alkaline earth metal hydroxide as well as the chloroacetic acid in the form of aqueous solutions, making special, expensive dosing devices for pulverulent compounds superfluous. It is sufficient to provide the alcohol or ether alcohol in a suitable agitated vessel and to introduce the aqueous chloroacetic acid and the aqueous alkali metal solution via separate feed conduits into the agitated vessel under agitation within a temperature range of about 60°–140° C., preferably 60°–120° C., and under a pressure of about 10–100 mbar.

Suitably, the chloroacetic acid should be used as a 60–90%, preferably about an 80% aqueous solution (commercially available), and the alkali hydroxide solution as a 40–70%, preferably about a 50% aqueous solution, both by weight. These are preferably conveyed by means of metering pumps. In this connection, the hydroxide solution should be added in metered amounts of the stoichiometric quantity, based on the amount of chloroacetic acid preferably, one OH-equivalent of the hydroxide being necessary for neutralising the acid and one for substituting the chlorine atom of the chloroacetic acid according to the equations:

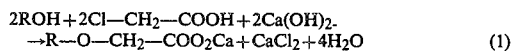

$$2ROH + 2Cl-CH_2-COOH + 2Ca(OH)_2 \rightarrow R-O-CH_2-COO_2Ca + CaCl_2 + 4H_2O \quad (1)$$

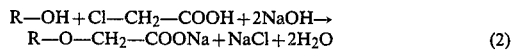

$$R-OH + Cl-CH_2-COOH + 2NaOH \rightarrow R-O-CH_2-COONa + NaCl + 2H_2O \quad (2)$$

The amount of chloroacetic acid will be 0.5–1 times the stoichiometric quantity based on the amount of alcohol or phenol, preferably the stoichiometric amount itself. Although the hydroxide solution and the chloroacetic acid solution are added simultaneously, it has proved to be expedient to begin feeding the hydroxide solution with a small lead time, e.g., about 5–10 minutes before adding the chloroacetic acid. This ensures that during the course of the reaction there is always a small excess of alkali, which disappears toward the end of the reaction. Suitable bases that can be used are: an aqueous $Ca(OH)_2$ suspension, etc., solutions of NaOH, KOH, etc. or mixtures of these bases.

The necessary, optimum water concentration in the reaction mixture is 0.30 to 1.5% by weight, e.g., 0.3 to 1.25% by wt., preferably in the range from 0.3 to 0.8, e.g., 0.4 to 0.8% by weight. It is readily possible to set an advantageous value for the amount of water by selecting the parameter pair of pressure and temperature; in this connection, increased pressure is to be combined with higher temperature. For example, the reaction can be conducted under a pressure of 12 mbar and at a temperature of 70° C. with the same result as that obtained under a pressure of 25 mbar and at 90° C. Equivalent combinations can be routinely determined by conventional considerations, perhaps with a few routine preliminary experiments. Similarly, other equivalent combinations corresponding to other amounts of water can be routinely determined.

The feed rate can be chosen within a wide range (cf. Examples 3 and 3a, Table I herein) provided that the amount of water introduced with the aqueous solutions is removed from the reaction mixture with sufficient speed and amount so that the water concentration of this invention of 0.3–1.5% by weight can be maintained. Overall reaction times are usually 180–360 min.

The reaction is suitably conducted in a cylindrical agitated vessel equipped with a flat paddle mixer. Preferably, the vessel has a double jacket so that the required reaction temperature can be maintained by cooling or heating. In the lower drain of the reaction vessel, product is withdrawn in a small amount via a T-member, for example using a geared pump, and recycled into the upper portion of the reactor. This provides the capability of taking and analyzing samples during the conductance of the reaction without interrupting the vacuum. For example, the secondary stream can be conducted continuously through a measuring zone recording the water content. The hydroxide solution and the chloroacetic acid can be fed from dropping funnels, but exactly operating metering pumps are advantageously employed.

The conduits for feeding, e.g., sodium hydroxide solution, on the one hand, and chloroacetic acid, on the other hand, can be immersed in the provided oxethylate or other starting alcohol or phenol. The main quantity of the water withdrawn can be condensed and separated by way of an effective cooler; the remainder—if necessary—can be removed via well-cooled cooling traps. Any organic material which may have been entrained can be separated in a separator and recycled. The reaction is practically finished once the chloroacetic acid and sodium or other hydroxide solutions have been added in their entirety; this can be determined by an extensive consumption of sodium hydroxide solution. For this reason, a brief follow-up agitation phase of a few minutes is sufficient. All of these procedures are conventional.

The further working-up procedure to which the thus-prepared product is subjected depends on the end use desired. For certain uses, for example for tenside flooding, it is possible to employ the resultant crude product directly. In such case, it is unnecessary to separate the sodium chloride formed as a by-product. However, if such a separation is desired, it is possible to obtain separation, by acidifying the reaction mixture and heating it to about 95° C., into an organic upper phase containing the free acid, which can be easily separated from the lower, aqueous phase containing the sodium chloride in dissolved form (cf. U.S. Pat. No. 3,992,443, column 4, lines 6–11).

Compounds lending themselves to carboxymethylation by the present process include: saturated or unsaturated, straight-chain or branched aliphatic alcohols of 8–20, carbon atoms, e.g., n-octanol, 2-ethylhexanol, capryl alcohol, n-decanol, lauryl alcohol, myristyl alcohol, cetyl alcohol, stearyl alcohol, eicosyl alcohol, or oleyl alcohol, etc.; similar thioalcohols, such as, for example, lauryl mercaptan, decyl mercaptan, myristyl mercaptan, or stearyl mercaptan; alkyl phenols of 7–18 carbon atoms in the alkyl portion, such as, for example, cresol, ethylphenol, propylphenol, butylphenol, pentylphenol, hexylphenol, heptylphenol, octylphenol, nonylphenol, decylphenol, undecylphenol, or dodecylphenol, etc.; or dialkyl phenols of 7–18 C-atoms in each alkyl portion, e.g. dinonylphenol, etc.; and furthermore the oxethylation products of the aforementioned alcohols, thioalcohols, and alkyl phenols with 1–40 ethylene oxide groups, preferably 1–30, especially 2–15 ethylene oxide groups. The oxethylated reactants are fully conventionally prepared, e.g., as disclosed in Ullmanns Encyclopädie der technischen Chemie, Volume 22, page 489, Verlag Chemie GmbH, Weinheim (1982), whose disclosure is incorporated by reference herein and are largely commercially available.

If the thus-formed reaction product is a compound which is solid at the reaction temperature (such as, for example, when myristyl alcohol is carboxymethylated, Example 9 herein), then the mixture in some cases can no longer be stirred. In this case, the compound to be carboxymethylated can be used in large excess (based on chloroacetic acid) and thus can take over simultaneously the function of a solvent or diluent.

Sodium hydroxide as an aqueous 50% strength solution will usually be employed as the base. It is likewise possible without difficulty to utilize other bases, e.g. potassium hydroxide, or also mixtures of potassium hydroxide and sodium hydroxide as aqueous solutions. The reaction can, of course, also be conducted continuously.

The products of the process of this reaction can be used, e.g., in the processes disclosed in U.S. application Ser. Nos. 300,427 (Sept. 9, 1981), 300,547 (Sept. 9, 1981), 349,947 (Feb. 18, 1982), 349,945 (Feb. 18, 1982) and 413,908 (Sept. 4, 1982), all of whose disclosures are incorporated by reference herein.

The term "degree of carboxymethylation" employed in the following examples is defined as $$\frac{\text{moles of carboxylate obtained} \times 100}{\text{moles of (thio)alcohol, phenol or oxylate used}}$$

When working with a less than stoichiometric amount of chloroacetic acid, based on the (thio)alcohol, phenol or oxethylate utilized, in order to attain lower degrees of carboxymethylation (cf. Examples 8 and 10) or for reasons of process technology (Example 9), then a valuable measure for the quality of the reaction in addition to the degree of carboxymethylation, is also the selectivity of the reaction based on the amount of chloroacetic acid employed (and in each case also completely converted).

The carboxylate content is determined by means of a two-phase titration with chloroform as the extractant and safranine as the indicator, by titration with cetyl pyridinium chloride.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A cylindrical agitator-equipped vessel having a capacity of 6.5 l and a diameter of 150 mm was charged with 2,420 g (5 moles) of nonylphenol oxethylated with 6 moles of ethylene oxide ("MARLOPHEN 86 S"). The reaction vessel, provided with a double jacket, is heated by way of a thermostat to 70° C., and a reaction pressure is set of 12 mbar. The content is stirred with a highly effective flat paddle agitator (about 700 rpm). At the bottom of the reactor, product is withdrawn from the latter by means of a geared pump, and this product is recycled into the upper portion of the reactor. Samples can be taken from this product circulation without interrupting the vacuum. By way of accurately operating metering pumps, 600 g of an 80% aqueous solution of monochloroacetic acid (5 moles) (chloroacetic acid with a concentration of about 99%) and 808 g of a 49.5% aqueous solution of sodium hydroxide (10 moles) are fed separately to the reactor within 3 hours. It is advantageous to start feeding the alkali solution about 5–10 minutes earlier than the chloroacetic acid; due to this feature, an alkaline reaction is ensured in the reactor at all times.

The water introduced and the water formed during the reaction is removed by means of an adequately dimensioned vapor pipe, condensed to the largest part by way of a cooler, and the remainder is deposited in cooling traps arranged downstream thereof. After a reaction period of 60 (120, 180) minutes, a sample taken from the reactor has the following analytical data (in weight percent):

| RCOONa$^{(+)}$ | NaCl | NaOH | H$_2$O | RCOONa$^{(++)}$ | Time (min) |
| --- | --- | --- | --- | --- | --- |
| 34.9 | 3.6 | 0.6 | 0.42 | 36.6 | 60 |
| 64.4 | 7.0 | 0.6 | 0.65 | 70.2 | 120 |
| 87.2 | 9.4 | 0.5 | 1.0 | 97.9 | 180 |
| 88.5 | 9.9 | 0.04 | 0.27 | 98.7 | 200 |

$^{(+)}$molecular weight 564
$^{(++)}$calculated without secondary components (NaCl, NaOH, H$_2$O)

During the subsequent follow-up stirring period under vacuum (20 minutes), the carboxylate content in the reaction mixture rises slightly to 88.5%. The amount of reaction product obtained in total is 3,137 g. This yields, by calculation, a content of 2,776 g of carboxymethylated compound (4.92 moles). The chloroacetic acid employed (5.0 moles), which has been completely converted, is thus reacted with a selectivity of 98.4% during the carboxymethylation reaction while the degree of carboxymethylation of the oxethylate employed amounts to 98.4%.

Comparative Example 1

Example 1 is repeated, but the reaction pressure is set at 65 mbar and the reaction temperature at 75° C. An average water content of 1.7% by weight is obtained in the reaction mixture. A content of 78.2% by weight of carboxymethylated product is obtained (2,443 g), corresponding to a degree of carboxymethylation of 87%.

COMPARATIVE EXAMPLE 1a

In this example, pressure and temperature conditions and accordingly also the water content of Japanese Application No. Sho-50-24 215 are maintained.

Comparative Example 1 is repeated, but 2,420 g (5 moles) of oxethylated nonylphenol (with 6 ethylene oxide) is provided and mixed with 595 g of sodium chloroacetate (5 moles, 98% strength). Thereafter, 407 g of sodium hydroxide solution (5 moles, 49.2% strength) is fed into the reaction mixture with the aid of a metering pump during the course of three hours under agitation at a temperature of 75° C. and under a pressure of 65 mbar. A water content is obtained of between 1.5 and 1.7% by weight in the reaction mixture. After terminating the feed of sodium hydroxide solution, agitation is continued for 20 minutes while maintaining the reaction pressure of 65 mbar, and after elimination of the vacuum after another 10 minutes, the reaction product is analyzed. A carboxymethylate content of merely 58.5% is found (1,835 g ≙ 3.25 moles), from which a degree of carboxymethylation is calculated of 65%.

Example 1, Comparative Examples 1 and 1a show that the water content in the reaction mixture must be <1.25% by weight to obtain an almost quantitative carboxymethylation of the oxethylate, and that the simultaneous addition of aqueous sodium hydroxide solution and aqueous chloroacetic acid considerably improves the degree of conversion.

EXAMPLES 2-6

The procedure of Example 1 is repeated in the following Examples 2-6, but operating at a reaction temperature of 90° C. The reaction pressure is varied, thus obtaining a differing water content of 0.4-1.5% by weight. In this connection, it is found that a degree of carboxymethylation of 95-99% is obtained with a water content of 0.4-0.8% by weight (Examples 2, 3, 4); about 90% is still obtained with a water content of 1.3% by weight (Example 5), and with a still higher water content (Example 6), the degree of carboxymethylation drops below 90%. In Example 3a, the dropwise feeding period for chloroacetic acid and for sodium hydroxide solution, amounting to three hours in all other examples, is reduced to 1.5 hours, which is possible without impairment with respect to the degree of carboxymethylation to be attained (cf. Examples 3 and 3a).

TABLE I

| Example | 2 | 3 | 3a(+) | 1 | 4 | Not According to Invention | |
|---|---|---|---|---|---|---|---|
| | | | | | | 5 | 6 |
| Pressure mbar | 12 | 25 | 25 | 12 | 50 | 75 | 100 |
| Temp. ° C. | 90 | 90 | 90 | 70 | 90 | 90 | 90 |
| Water Content % by Wt. | 0.45 | 0.58 | 0.55 | 0.65 | 0.80 | 1.30 | 1.52 |
| RCOONa | 89.4 | 88.2 | 88 | 88.5 | 85.6 | 80.6 | 78.6 |

TABLE I-continued

| Example | 2 | 3 | 3a(+) | 1 | 4 | Not According to Invention | |
|---|---|---|---|---|---|---|---|
| | | | | | | 5 | 6 |
| % by Wt. in Final Product | | | | | | | |
| Degree of Carboxymethylation % | 99.4 | 98.1 | 97.9 | 98.4 | 95.2 | 89.7 | 87.4 |

(+)Time of dropwise addition of alkali solution and chloroacetic acid: 1.5 hours; in all other examples, 3 hours.

EXAMPLE 7

The apparatus described in Example 1 was charged with 2,420 g of nonylphenol (5 moles), oxethylated with 6 moles of ethylene oxide; and within three hours, in the way indicated above, 600 g of an 80% aqueous solution of chloracetic acid (5 moles), as well as a mixture consisting of 404 g of a 49.5% aqueous sodium hydroxide solution and 561 g of a 50% aqueous potassium hydroxide solution (respectively 5 moles of each base) was introduced under a reaction pressure of 12 mbar and at a reaction temperature of 80° C. While feeding the aqueous alkali solution and the aqueous chloroacetic acid, a water content of 0.57% by weight is obtained in the reaction mixture. The light-colored final product is stirred for another 30 minutes at the reaction temperature after terminating the addition of the reaction components.

| RCOONa/K | 88.1% by weight |
|---|---|
| NaCl/KCl | 10.8% by weight |
| NaOH | 0.01% by weight |
| $H_2O$ | 0.20% by weight |

A content of 4.92 moles of Na/K carboxylate mixture (MW $\overline{572}$) is calculated from the analytical data of the end product (3,193 g), i.e. the degree of carboxymethylation is 98.4%.

EXAMPLE 8

A 100-liter agitator-equipped reactor is charged with 23.79 kg of a nonylphenol oxethylated with 6.1 moles of ethylene oxide/mole (48.71 moles). The reactor is heated to a temperature of 90° C. and evacuated to a pressure of 18-20 mbar. Under vigorous agitation, 4 26 kg of chloroacetic acid, 99% strength, in the form of an approximately 80% aqueous solution (44.6 moles) and 7.3 kg of an aqueous 49% strength sodium hydroxide solution (89.2 moles) are introduced analogously to Example 1 within three hours by way of separate feed conduits immersed in the charged nonylphenol oxethylate.

The water is removed from the reactor via an adequately dimensioned, heated vapor conduit (diameter 70 mm) and condensed by way of coolers. In total, 7.07 kg of water is condensed. The water content in the reaction mixture during the metered feeding of the alkali solution and chloroacetic acid fluctuates between 0.6 and 0.7% by weight. After the chloroacetic acid solution and sodium hydroxide solution have been added, the reaction product is stirred for another 20 minutes under the indicated reaction conditions and then discharged from the reactor in the warm state.

The final product (30.01 kg) has the following analytical data:

| | |
|---|---|
| RCOONa (MW 568) | 81.6% by weight |
| NaCl | 9.2% by weight |
| NaOH | 0.04% by weight |
| H$_2$O | 0.26% by weight |

A degree of carboxymethylation of 88.7% can be calculated therefrom. Since the molar ratio of chloroacetic acid to oxethylate equals 44.6/48.71, corresponding to 0.916, the chloroacetic acid employed is consumed with a selectivity of 96.9% for the carboxymethylation reaction.

EXAMPLE 9

2,568 g of C$_{14}$-alcohol (12 moles) ("ALFOL 14 RD") is reacted with 670 g of monochloroacetic acid (99% strength=7 moles), dissolved in 167 g of water, as well as 1,135 g of a 49.3% aqueous sodium hydroxide solution (14 moles) during the course of four hours at a temperature of 95° C. and under a pressure of 25 mbar in the apparatus disclosed in Example 1. A water content of 0.65% by weight is thus obtained in the reaction mixture. Of the alcohol present in excess, 98 g is distilled off during the reaction together with the water vapor. After the addition of the alkali solution and chloroacetic acid is completed, stirring is continued for another hour under normal pressure.

The resultant, light colored reaction product (3,447 g) contains 54.3% by weight of the carboxymethylated alcohol and 0.2% by weight of water. From this, an amount of 1,872 g (6.37 moles) of carboxylate (MW 294) is calculated. Based on the 7 moles of chloroacetic acid utilized, the latter is reacted with a selectivity of 91%.

EXAMPLE 10

2,064 g of C$_{12/18}$-alcohol oxethylated with 3 moles of ethylene oxide (6 moles) is charged into the apparatus described in Example 1. A solution is prepared from 4.8 moles (458 g) of a 99% strength chloroacetic acid in 1,150 g of water, and this solution is fed, analogously to Example 1, with 781 g of 49.2% sodium hydroxide solution (9.6 moles) in metered quantities into the oxethylate during the course of three hours with agitation under a pressure of 26 mbar and at a temperature of about 82° C. A sample, analyzed after a reaction period of 1.5 hours, shows a water content in the reaction mixture of 0.74% by weight.

After completion of the feeding of alkali solution and chloroacetic acid solution, the mixture is further stirred for 20 minutes under the reaction conditions to finish the reaction. The final product (2,690 g) has the following analytical data:

| | |
|---|---|
| RCOONa (MW 424) | 70.1% by weight |
| NaCl | 10.4% by weight |
| NaOH | 0.43% by weight |
| H$_2$O | 0.62% by weight |

A degree of carboxymethylation of 74.1% can be calculated from these data. The chloroacetic acid utilized is reacted with a selectivity of 92.6%. Based on the selected molar ratio of 1:0.8, the highest degree of carboxymethylation attainable would be 80%.

EXAMPLE 11

The apparatus disclosed in Example 1 is charged with 2,986 g of dinonylphenol oxethylated with 9.1 moles of ethylene oxide (4 moles). During the course of two hours, 478 g of an 80% aqueous chloroacetic acid (4 moles) and 647 g of a 49.5% aqueous sodium hydroxide solution (8 moles) are introduced into the reactor analogously as described in Example 1. During this step, a pressure is set of 22–25 mbar and a temperature is set of about 90° C. The stirrer speed is about 700 rpm. The water content thus obtained in the reaction mixture reaches a value of 0.5% by weight. After completion of the feeding of alkali solution and chloroacetic acid, the mixture is stirred for another 20 minutes under a pressure of 22 mbar and at a temperature of 90° C. The yellowish final product (3,558 g), still flowable at room temperature, shows the following analytical values:

| | |
|---|---|
| RCOONa (MW 827) | 84.0% by weight |
| NaCl | 7.3% by weight |
| NaOH | 0.02% by weight |
| H$_2$O | 0.51% by weight |

An amount of 2,988 g (3.61 moles) of carboxymethylated compound, and a degree of carboxymethylation of 90.3% are calculated from these data.

EXAMPLE 12

The apparatus of Example 1 is charged with 1,508 g (3 moles) of "MARLOPHEN 814" (nonylphenol oxethylated with 14 moles of ethylene oxide, MW 836). During the course of 1.5 hours, 359 g of chloroacetic acid (80% aqueous solution, 30 moles) and 488 g of a 49.2% sodium hydroxide solution (6 moles) are fed with agitation under a pressure of 25 mbar and at a temperature of 90° C. The water content in the reaction mixture is 0.58% by weight. After completion of the addition of sodium hydroxide solution and chloroacetic acid, the mixture is further agitated for another 20 minutes under unchanged reaction conditions. The resultant end product (2,939 g) has the following analytical data:

| | |
|---|---|
| RCOONa (MW 916) | 87.7% by weight |
| NaCl | 6.4% by weight |
| NaOH | 0.03% by weight |
| H$_2$O | 0.5% by weight |

A degree of carboxymethylation of 93.8% is calculated from the indicated values.

Example 13

As described in Example 1, 2,500 g (6.61 moles) of lauryl mercaptan, oxethylated with 4 moles of ethylene oxide, is reacted with 583 g (6.1 moles) of chloroacetic acid (concentration 99%), present as an 80% aqueous solution, dissolved in water, and with 985 g (12.2 moles) of an aqueous 49% strength sodium hydroxide solution. The reaction temperature is 75° C., the reaction pressure is 12 mbar. During the metered feeding of the components, a water content of 0.62% by weight is obtained in the reaction vessel. The feeding is completed after three hours; stirring is then continued for another 20 minutes under the reaction conditions. In the reactor remains 3,368 g of a final product having the following analytical data:

| RCOONa (MW 458) | 78.1% by weight |
| NaCl | 12.1% by weight |
| NaOH | 0.01% by weight |
| H$_2$O | 0.53% by weight |

From these data, a quantity of 2,630 g of carboxymethylated compound is calculated (5.74 moles), yielding a degree of carboxymethylation of 86.8%. Since the molar ratio of the compounds employed is merely 1:0.923, a degree of carboxymethylation of maximally 92.3% could have been attainable at best; consequently, the determined degree of carboxymethylation of 86.8% corresponds to a selectivity of $$\frac{5.74 \times 100}{6.10} = 94.1\%,$$

based on the reacted chloroacetic acid.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the production of a carboxymethylated (thio)alcohol, (thio)alcohol ether, alkyl phenol or alkyl phenol ether, comprising simultaneously adding an aqueous solution of up to a stoichiometric quantity of monochloroacetic acid based on the amount of alcohol or phenol compound, and a separate aqueous solution of about twice the stoichiometric amount of an alkali or alkaline earth metal hydroxide, based on the amount of monochloroacetic acid, under agitation, at a temperature of about 60°–140° C. and under a pressure of about 10–100 mbar, to a starting compound which is a saturated or unsaturated, aliphatic (thio)alcohol of 8-20 carbon atoms, a (di)-C$_{7-18}$-alkyl phenol or such a (thio)alcohol or phenol compound which has been oxethylated with 1-40 ethylene oxide units, while maintaining the water content in the reaction mixture in the range of 0.3–1.25% by weight of the total mixture, throughout the reaction period.

2. A process of claim 1, wherein the water content in the reaction mixture is 0.3–0.8% by weight.

3. A process of claim 1, wherein the hydroxide is an alkali metal hydroxide.

4. A process of claim 3, wherein the hydroxide is sodium hydroxide.

5. A process of claim 2, wherein the hydroxide is an alkali metal hydroxide.

6. A process of claim 2, wherein the hydroxide is sodium hydroxide.

7. A process of claim 1, wherein the concentration of monochloroacetic acid in the aqueous solution is about 80 wt. % and the concentration of hydroxide compound in the aqueous solution is about 50 wt. %.

8. A process of claim 1, wherein the addition of the aqueous hydroxide solution begins before the addition of the aqueous monochloroacetic acid solution.

9. A process of claim 1, wherein the water content during the entire reaction is 0.4 to 0.8 wt. %.

10. A process of claim 1, wherein water is continuously removed during the reaction.

11. A process of claim 1 further comprising separating the carboxymethylated product from the reaction medium.

12. A process of claim 1, wherein the starting material is n-octanol, 2-ethylhexanol, capryl alcohol, n-decanol, lauryl alcohol, myristyl alcohol, cetyl alcohol, stearyl alcohol, eicosyl alcohol, or oleyl alcohol.

13. A process of claim 1, wherein the starting material is lauryl mercaptan, decyl mercaptan, myristyl mercaptan, or stearyl mercaptan.

14. A process of claim 1, wherein the starting material is cresol, ethylphenol, propylphenol, butylphenol, pentylphenol, hexylphenol, heptylphenol, octylphenol, nonylphenol, decylphenol, undecylphenol, dodecylphenol, or dinonylphenol.

15. A process of claim 1, wherein the starting material is a compound oxyethylated with 1–30 ethylene oxide groups.

16. A process according to claim 1, wherein the temperature is 70° C. or above.

17. A process according to claim 1, wherein the yield of carboxymethylated(thio) alcohol, (thio) alcohol ether, alkyl phenol or alkyl phenol ether is above 90%.

* * * * *